(12) United States Patent
Kalmann et al.

(10) Patent No.: US 6,328,749 B1
(45) Date of Patent: *Dec. 11, 2001

(54) REMOTE ENDARTERECTOMY RING STRIPPER

(75) Inventors: Menno Kalmann, PD Elspect; Franciscus Laureus Moll, La Bosch en Duin, both of (NL); Thomas J. Fogarty, Portola Valley, CA (US); Kenneth Mollenauer, Los Gatos, CA (US); Brian A. Glynn, Santa Rosa, CA (US); Richard O. Murphy, Mountain View, CA (US); Jay A. Lenker, Laguna Beach, CA (US); Brian J. Cox, Cupertino, CA (US)

(73) Assignee: Vascular Architects, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/169,211

(22) Filed: Oct. 9, 1998

Related U.S. Application Data

(63) Continuation-in-part of application No. 08/633,730, filed on Jun. 10, 1996, now Pat. No. 5,843,102.

(30) Foreign Application Priority Data

Oct. 25, 1993 (NL) ...................................... 9301842

(51) Int. Cl.⁷ .................................................. A61B 17/22
(52) U.S. Cl. .......................................................... 606/159
(58) Field of Search .................................. 606/113, 110, 606/159, 174

(56) References Cited

U.S. PATENT DOCUMENTS

| | | | |
|---|---|---|---|
| 777,716 | * 12/1904 | Dennett | ................................ 606/113 |
| 856,927 | * 6/1907 | Straw | ................................... 606/110 |
| 1,167,014 | 1/1916 | O'Brien . | |
| 2,944,552 | 7/1960 | Cannon . | |

(List continued on next page.)

FOREIGN PATENT DOCUMENTS

| | | |
|---|---|---|
| 0119688 | 9/1984 | (EP) . |
| 0274846 | 7/1988 | (EP) . |
| 2635962 | 3/1990 | (FR) . |
| 2195540A | 4/1988 | (GB) . |
| 673-273 | 7/1979 | (SU) . |
| 1526-662A | 12/1989 | (SU) . |
| WO 90/01969 | 3/1990 | (WO) . |
| WO 94/04096 | 3/1994 | (WO) . |

OTHER PUBLICATIONS

Ho, G. et al., "The Mollring Cutter™ Remote Endarterectomy: Preliminary Experience With a New Endovascular Technique For Treatment of Occlusive Superficial Femoral Artery Disease," *Journal of Endovascular Surgery*, 2(3):278–287 (1995).

Joosten, H. et al., "The Mollring Cutter™ Remote Endarterectomy," *Clinical Ischaemia*, 6(1):14–20 (in existence as of May 30, 1996).

Remote endarterectomy using the ring strip cutter technique (in existence as of May 31, 1996).

*Primary Examiner*—Michael H. Thaler
(74) *Attorney, Agent, or Firm*—James F. Hann; Haynes Beffel & Wolfeld

(57) ABSTRACT

A remote endarterectomy ring stripper (1) includes an elongate shaft (8), having distal (36) and proximal (32) ends, an intima stripping ring (4, 34) mounted to the distal end of the elongate shaft and an intima cutter assembly having an intima cutting element (22, 42, 56, 60), at the stripping ring, operated by a user-operated cutting element actuator (10; 12, 50). Movement of the cutting element severs a length of intima (26), which has been separated from the wall (28) of the blood vessel (23), passing through the stripping ring.

27 Claims, 5 Drawing Sheets

U.S. PATENT DOCUMENTS

| | | |
|---|---|---|
| 3,448,741 | 6/1969 | Dennis et al. . |
| 3,564,582 | 2/1971 | Wai . |
| 3,837,345 | 9/1974 | Matar . |
| 4,030,503 | 6/1977 | Clark, III . |
| 4,287,890 | 9/1981 | Fogarty . |
| 4,290,427 | 9/1981 | Chin . |
| 4,315,511 | 2/1982 | Chin . |
| 4,559,927 | 12/1985 | Chin . |
| 4,574,781 | 3/1986 | Chin . |
| 4,594,996 | 6/1986 | Ibrahim et al. . |
| 4,621,636 | 11/1986 | Fogarty . |
| 4,655,217 | 4/1987 | Reed . |
| 4,665,918 | 5/1987 | Garza et al. . |
| 4,706,671 | 11/1987 | Weinrib . |
| 4,765,332 | 8/1988 | Fischell et al. . |
| 4,887,613 | 12/1989 | Farr et al. . |
| 4,994,067 | 2/1991 | Summers . |
| 5,071,424 | 12/1991 | Reger . |
| 5,100,423 | 3/1992 | Fearnot . |
| 5,133,725 | 7/1992 | Quadri . |
| 5,171,316 | 12/1992 | Mehigan . |
| 5,366,463 | 11/1994 | Ryan . |
| 5,409,454 | 4/1995 | Fischell et al. . |
| 5,480,379 | 1/1996 | LaRosa . |
| 5,820,629 * | 10/1998 | Cox ................................ 606/159 |

\* cited by examiner

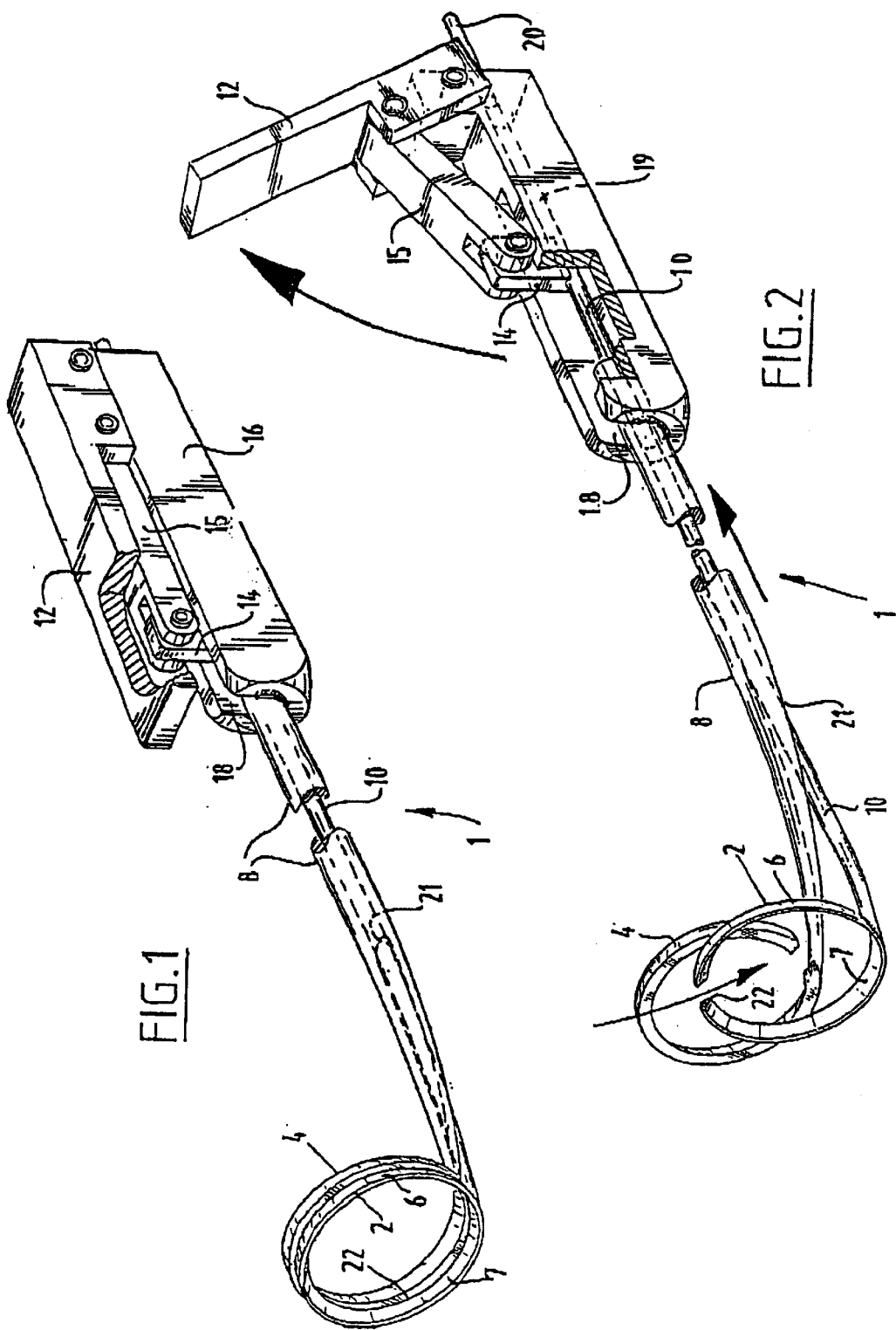

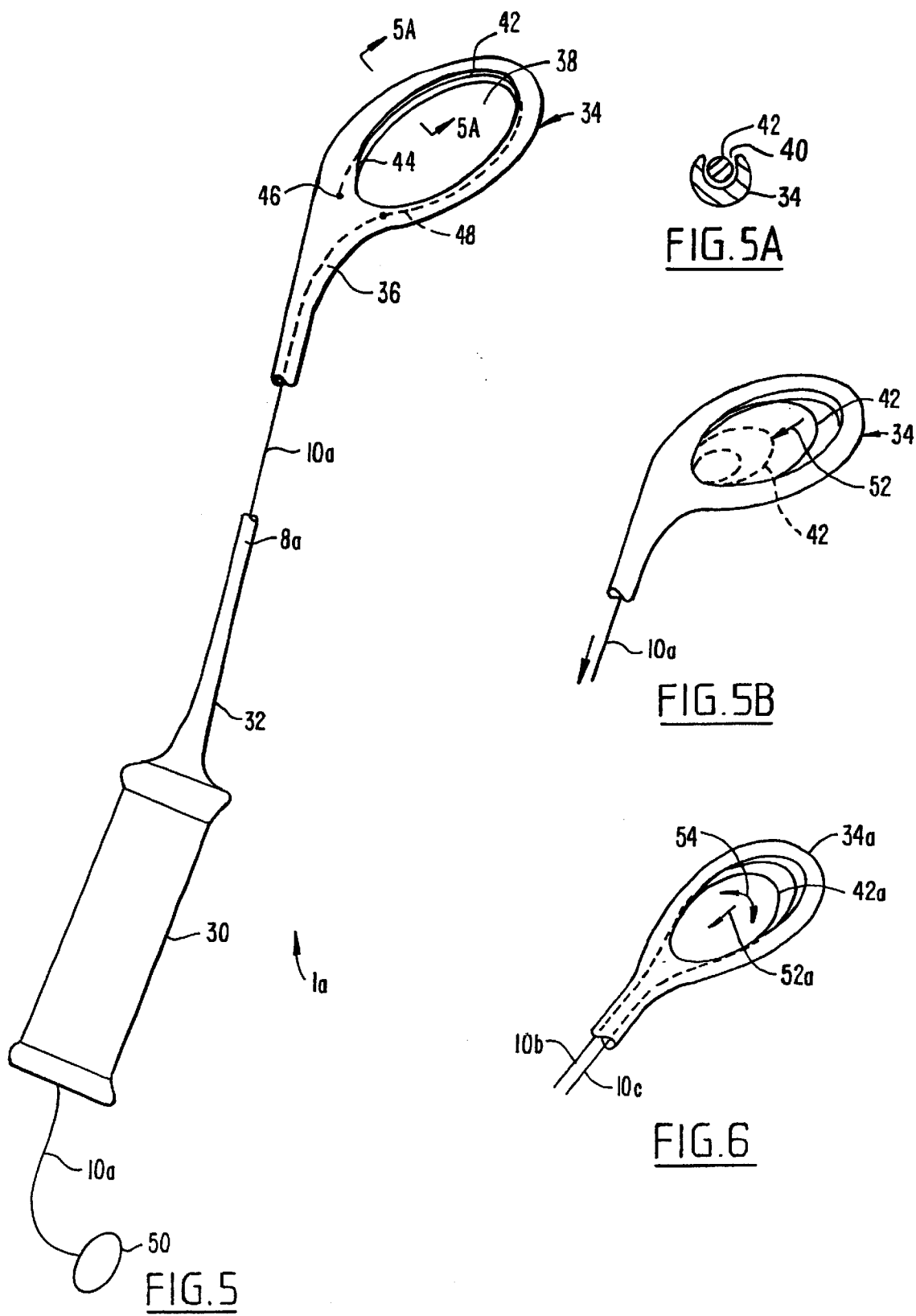

REMOTE ENDARTERECTOMY RING STRIPPER

CROSS-REFERENCE TO RELATED APPLICATIONS

This application is a continuation-in-part patent application of U.S. patent application Ser. No. 08/633,730 filed Jun. 10, 1996, now U.S. Pat. No. 5,843,102, which is the national phase application of International Application No. PCT/NL94/00254, entitled "AN INSTRUMENT FOR LOOSENING AND CUTTING THROUGH THE INTIMA OF A BLOOD VESSEL AND A METHOD THEREFOR," international filing date Oct. 18, 1994, published May 4, 1995, which claims the benefit of NL 9301842, filed Oct. 25, 1993, the disclosures of which are incorporated by reference.

BACKGROUND OF THE INVENTION

This invention relates to a device or assembly for the treating of blood vessels and more specifically to a device or assembly for performing a remote endarterectomy or dilatation and to an endarterectomy method using the device.

It is known that narrowing or blockages (thromboses) can occur in blood vessels, particularly in older people. This is often caused by the effects of deposits on the inside walls of the blood vessels leading to hardening or calcifying of the blood vessels. This has dangerous consequences for the health, because the quantity of blood now able to flow through the blood vessel is drastically reduced. In order for effective blood circulation to occur, and to avoid possible limb amputation for example, any blockage or obstacle in the blood vessels must be removed.

One conventional method for treating hardening of the blood vessels involves a complicated operation. In the case of the artery between the groin and knee, this is quite a severe operation. The patient is cut open at the groin and the knee, whereafter the artery is completely removed and replaced by an artificial artery. This can be especially hard on and dangerous for older people, particularly because of the duration of the operation. The operation is also expensive and requires a lengthy hospital recovery period for the patient. Additionally, there is a danger of rejection of the artificial blood vessel by the body, which can lead to further post operation complications.

Another procedure for treating totally or partially blocked blood vessels, called endarterectomy, separates the inner layer of the blood vessel, the so called tunica-intima or intimal lining or intima, from the blood vessel wall using a ring stripper. The intimal lining, which has been separated from the vessel wall over the length of the blockage, is then removed from the patient along with the blockage. A new intimal lining then grows back to replace the removed intimal lining. See, for example, U.S. Pat. Nos. 2,944,552 and 4,621,636.

Conventional endarterectomy procedures are typically carried out using two incisions, one on either side of the blockage. The first incision permits access to the vessel by the instrument; the second incision permits access to the distal end of the separated intima so the separated intima may be severed from the vessel wall and then removed through the first incision.

SUMMARY OF THE INVENTION

The present invention is directed to a remote endarterectomy ring stripper which requires only one incision and provides for quicker, less expensive, more patient-friendly endarterectomy procedures.

The remote endarterectomy ring stripper includes an elongate shaft having distal and proximal ends. An intima stripping ring, having an open interior, is mounted to the distal end of the elongate shaft. The ring stripper also includes an intima cutter assembly having a cutting element and a cutting element actuator. The cutting element is located at the stripping ring and is movable along a cutting path across at least a portion of a cutting region. The cutting region passes through the open interior of the stripping ring.

The cutting element actuator has a first end, at the proximal end of the shaft, and a second end, operably coupled to the cutting element. The cutting element actuator is manipulated by the user to permit the user to cause the cutting element to move along the cutting path so to sever a length of intima, which has been separated from the wall of the blood vessel and passes through the open interior of the stripping ring.

The cutting element can take a number of different forms. In one embodiment the stripping ring is formed by a pair of stripping ring portions positioned adjacent to one another. The two stripping ring portions are movable with adjacent surfaces sliding against one another; the sliding surfaces have appropriately positioned cutting edges which sever the intima passing through the interior of the stripping ring. In another embodiment the cutting element includes an intima-severing wire initially positioned adjacent to the stripping ring; the cutting element is actuated by pulling on the wire to cause the wire to sever the intima passing through the stripping ring. Further embodiments use pivotal, retractable, or otherwise movable blades to cut the intima passing through the stripping ring. Still other types of cutting elements can be used as well.

A blocked blood vessel is able to be cleaned using the present invention so that the need for a time consuming, expensive bypass operation, which is harsh on the patient, is eliminated. The requirement of using an artificial replacement blood vessel is no longer present, because the old vessel is now in a state to again effectively fulfill its function. Therefore, rejection of an artificial blood vessel by the body, and its ensuing problems, do not play a role here. The hospital recovery period is shortened due to the less exacting nature of this operation, whereby the costs decrease and more hospital beds become available.

The stripping ring preferably has a cross section in the form of a truncated cone, the nose of which comprises a blunt edge which projects in the direction of the incision. In this way the blunt edge separates the intima from the blood vessel wall when the instrument is pushed between the intima and the blood vessel wall. The intima is thus peeled further away from the blood vessel wall and is subjected to a sort of bottle neck effect, caused by the cone form, between the two sides of the ring.

The length of the shaft may depend on the length of the blood vessel to be cleaned, and/or the extent of calcification in the blood vessel.

The cutting element actuator, in one embodiment, comprises a part that can take the form of a filament or a wire, that extends through the shaft, which can be moved with respect to the shaft by a user-actuated manipulator. In one embodiment the manipulator comprises a lever associated with the shaft. In this way the intima can be separated from the blood vessel wall and cut through at the required distance by the instrument, which is operable from outside the body.

The separation of the intima from the blood vessel wall and the cutting through and severing of the intima is consequently quick and able to be carried out in an elegant and simple manner. After cutting through of the intima, the intima plus blockage are removed through the single incision.

Further advantages, characteristics and details of the present invention will become clear from the following description which refers to the accompanying drawings.

BRIEF DESCRIPTION OF THE DRAWINGS

FIG. 1 is a partly broken away perspective view of a first embodiment of the invention;

FIG. 2 is a perspective view of the embodiment from FIG. 1, showing operation thereof;

FIG. 5 is an overall view of an alternative embodiment of the invention in which an intima-severing wire is initially housed within a groove formed within the stripping ring, the intima-severing wire being connected to an actuator wire which extends through the tubular shaft to a pull ring extending from the handle at the proximal end of the shaft;

FIG. 5A is a cross-sectional view taken along line 5A—5A of FIG. 5;

FIG. 5B is a simplified view illustrating the guillotine movement of the intima-severing wire within the stripping ring as the user pulls on the pull ring of FIG. 5;

FIG. 6 illustrates a further embodiment of the invention in which an actuator wire is connected to each end of the intima-severing wire so that pulling on one or both of the actuator wires causes the intima-severing wire to move as suggested in FIG. 5B, but also allowing a sawing action to be provided in addition to the guillotine action of FIG. 5B;

DESCRIPTION OF THE PREFERRED EMBODIMENT

Figure 3:
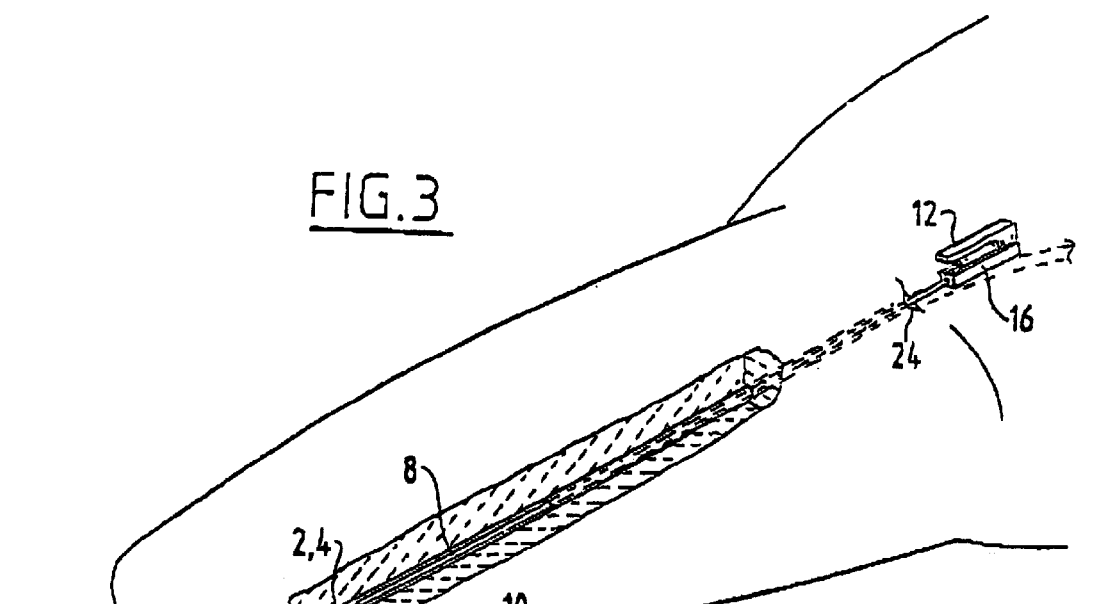
FIG. 3 is the embodiment from FIG. 1 applied to an embodiment of the method according to the present invention.

A first embodiment of a remote endarterectomy ring stripper 1, also referred to as instrument 1, according to the invention (FIG. 1) comprises two rings 2, 4 supported at an angle which are insertable around the intima, the front ring 2 having a blunt edge 6, a hollow shaft or pin 8, an actuator wire or a filament 10, movable in the hollow pin 8, which is connected via a hinge 15 of the lever 12 with a projection 14 of the filament 10, a grip part 16, which also acts as base for the lever 12, and a slot 18 in the grip part 16 wherein the projection 14 and the moveable part 10 extend. The hollow pin 8 is secured to the grip part 16, whilst the filament 10 moves in the slot 18. The slot 18 narrows to a narrower slot 19 (FIG. 2) which extends completely through the grip 16.

In FIG. 2, the lever 12 is in the raised position. On raising the lever 12, the filament 10 in the hollow pin 8 is displaced to the grip part 16, via the projection 14, so that a part 20 of the moveable part 10 moves through the channel 19 and projects out from the rearside of the grip part 16. On carrying out this action the front ring 2, which is supported by the moveable part 10, moves downwards with respect to the second ring 4, so that a scissor movement is obtained between the two rings 2, 4. The filament 10 extends out of the under side of the hollow pin 8 through an opening 21, whilst on the upper side the hollow pin 8 extends to the rings 2, 4.

The blunt edge 6 of the front ring 2 extends inwardly to a sharp inner edge 22 of the front ring 6 (FIGS. 1 and 2).

An instrument 1 according to the invention is inserted into the artery 23, see FIG. 3, via a small incision 24 of about 8–10 cm in the groin, between the groin and the knee, in such a way that the rings 2, 4 extend in the direction of the knee whilst the lever 12 and the grip part 16 are located outside of the body, near the incision 24 of the artery 23.

Figure 4:
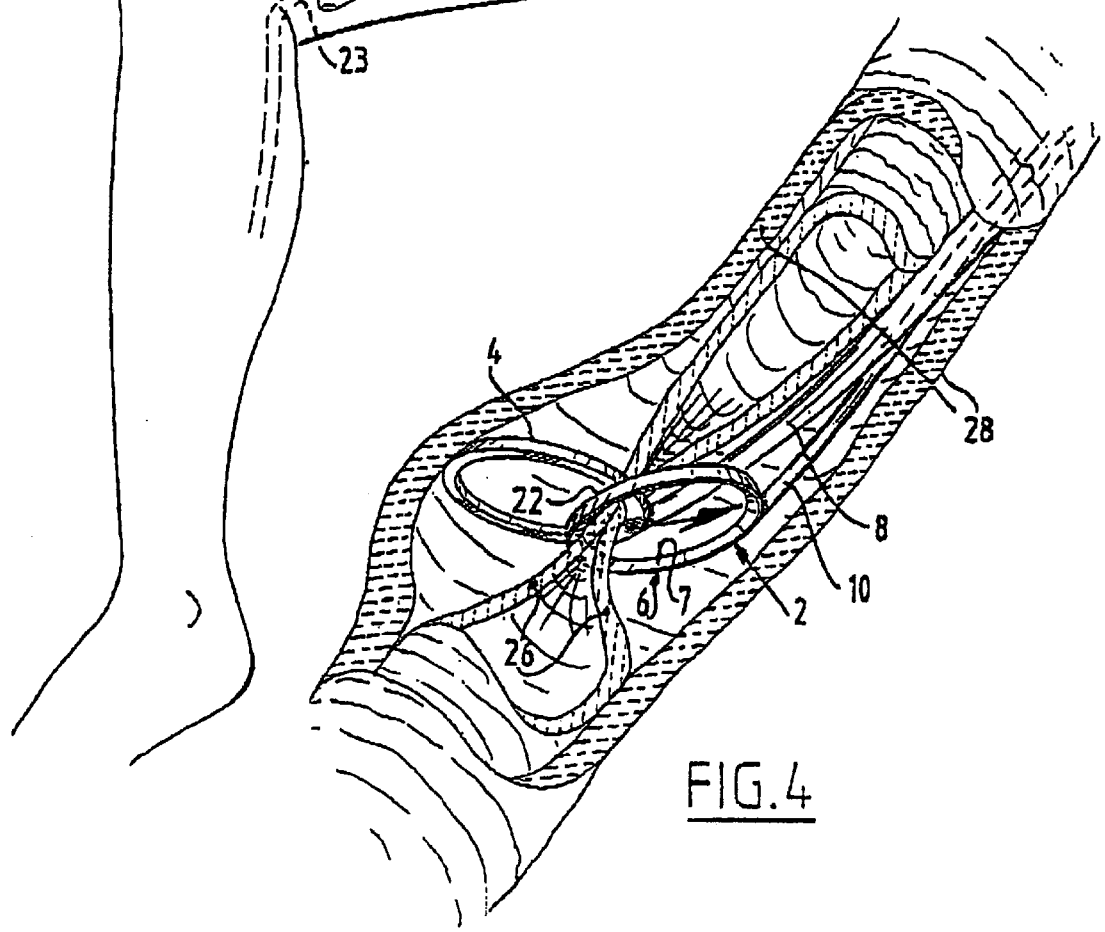
FIG. 4 is a detail of part of the embodiment from FIG. 1 in the action of cutting through an intima.

The front ring 2 is moved downwards with respect to the rear ring 4, by the scissor movement of the two rings 2, 4 (FIG. 4), causing the intima 26, which is already separated from the blood vessel wall 28, to be pinched between the two rings 2, 4. It is clear that further downward movement of the front ring 2 will result in the cutting through and severing of the intima 26 which is held between the sharp edge 22 of the front ring 2, supported by the hollow pin 8, and the rear ring 4, supported by the moveable part of filament 10.

The rings 2, 4 are preferably sharpened for about 40%, or 144° of their contours, front ring 2 sharpened along its upper inner side and rear ring 4 sharpened along its lower inner side, in order to achieve a highly efficient shear, scissor-like cutting movement when front ring 2 is moved relative to rear ring 4. This scissor-like cutting effect is particularly efficient in cutting through hardened, calcified material as relatively little mechanical force is needed in operation of the instrument, to effect a neat cut.

The rings 2, 4 are flattened where they meet, as shown in FIG. 2, in order to fit together as a single ring so that no obstructions project which could damage the outer layer of the blood vessel during insertion, operation and/or removal of the instrument.

From clinical tests it has been determined that an effective cutting through and severing is achieved when the rings are mounted at an angle of 45° relative to the filament and hollow pin. However, it will be obvious that the rings could be mounted in any direction and in any relative position in order to achieve efficient cutting.

At this angle of 45° it was found that the following ring diameters, with respect to the inner diameter of the blood vessel, yielded efficient separation of the intima from the blood vessel wall and cutting through the severing of the intima and any hardened, calcified material therein.

| Inner diameter blood vessel | diameter rings |
| --- | --- |
| 4 mm | 6.5 mm |
| 5 mm | 7.5 mm |
| 6 mm | 8.5 mm |
| 7 mm | 9.5 mm |
| 8 mm | 10.5 mm |
| 10 mm | 12.5 mm |

On inserting the instrument into an already opened blood vessel (FIGS. 3, 4) the front ring 2 and the rear ring 4 encircle the intima 26. The instrument is then pushed through the blood vessel. The blunt edge 6 of the front ring 2 separating the intima from the blood vessel wall 28, whereby the intima 26 is forced further inward away from the blood vessel wall by a funnel effect brought about by the front ring 2. After the two rings 2, 4 have been moved to a required distance in the blood vessel, for instance to a point where there is no more blockage of the blood vessel, the movement is stopped and the lever 12 is raised which brings about the earlier stated scissor movement for the cutting through and severing of the intima.

In order to further improve cutting and severing, at least one of the rings, preferably the front ring 2, may be vibrated during the scissor movement.

The intima and the blockage therein can be removed either by removing the instrument from the blood vessel or by any other way.

It will be noted that the present invention is not limited to the above-described embodiment of FIGS. 1–4. For instance in a further (not shown) embodiment of-the present invention the filament and hollow pin may be reversed so that the filament extends out of an opening on the upperside of the hollow pin, the position of the filament's and hollow pin's respective rings being reverse, whereupon cutting is achieved by pushing the filament instead of pulling the filament. In yet another (not shown) embodiment of the present invention, the hollow pin may be pushed to achieve a cutting movement, instead of pulling the filament.

A further advantage of the present invention is that blocked blood vessels, specifically the artery between the groin and the knee, can be unblocked to allow the insertion, via this artery, of a prosthetic into the aorta to treat patients who, along with blocked blood vessels, also have aneurysms for instance. For these patients the chest now no longer has to be opened in order to treat the aneurysm, as the now, unblocked artery between the knee and the groin yields a prosthetic access to the aorta.

FIGS. 5–11A illustrate alternative embodiments of the invention with corresponding reference numerals referring to corresponding structure. Ring stripper 1a, see FIGS. 5–5B, comprises a tubular shaft 8a having a handle 30 at the proximal end 32 of shaft 8a and a stripping ring 34 at the distal end 36 of shaft 8a. Stripping ring 34 and tubular shaft 8a are sized and configured to operate as an intima ring stripper in a generally conventional manner. Stripping ring 34 defines an interior 38 through which the severed intima 26 passes. Stripping ring 34 has a groove 40 along its inner circumference, see FIG. 5A, within which an intima-severing wire 42 is initially housed. Wire 42 can be temporarily maintained in groove 40 in a number of different ways, including magnetic attraction of wire 42 in groove 40, an expanding spring force biasing wire 42 into groove 40, snap fit of wire 42 in groove 40, releasable adhesive in groove 40, etc. One end 44 of wire 42 is fixed to stripping ring 34 at position 46 while the other end 48 is connected to an actuator wire 10a. Actuator wire 10a is connected at its proximal end to a pull ring 50. This permits the user to sever intima 26 passing through interior 38 of stripping ring 34 by pulling on pull ring 50 causing the intima-severing wire 42 to move in direction 52 of FIG. 5B from its initial position in groove 40 to a fully retracted position. Severing wire 42 is constructed to sever intima 26 by virtue of the size, shape, and surface character of the wire. For example, wire 42 could have a sharpened edge or diamond particles coating its surface.

FIG. 6 illustrates the distal end of an alternative embodiment of the invention in which stripping ring 34a houses an intima-severing wire 42a. However, both ends, 44a, 48a of wire 42a are connected to separate actuator wires 10b and 10c. Actuator wires 10b and 10c are connected to separate pull rings (not shown), and can be pulled in unison or alternatingly to create a pure guillotine action or a sawing action as indicated by arrows 52a, 54.

Figure 7:
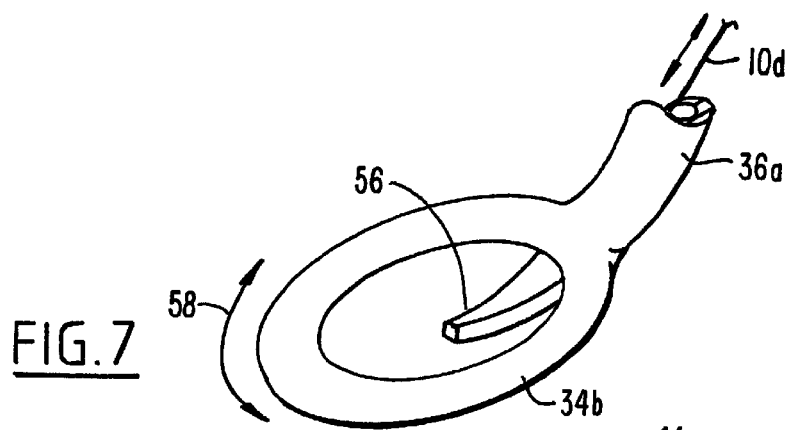
FIG. 7 illustrates a further embodiment of the invention in which a single retractable blade has been extended from the distal end of the hollow shaft to pierce the intima passing through the stripping ring, the intima being severed by rotating the stripping ring.
Figure 7A:
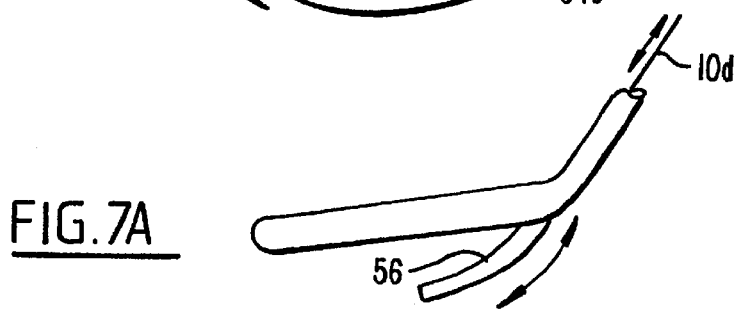
FIG. 7A is a side view of the embodiment of FIG. 7.

FIG. 7 shows an embodiment in which a retractable blade 56, normally housed within distal end 36a of the hollow shaft, can be extended out from the hollow shaft as shown in FIGS. 7 and 7A to pierce intima 26. To sever the intima, the instrument must be moved in a rotational motion over a total arc of about 360E, such as 180E in either direction from a start position, to completely sever intima 26 as indicated by arrow 58.

Figure 8:
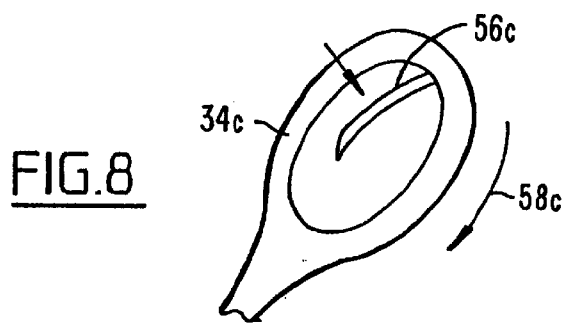
FIG. 8 illustrates a further embodiment of the invention in which a blade, pivotally mounted to the distal end of the stripping ring, is actuated to pivot across the interior of the stripping ring, after which the user rotates the stripping ring to completely sever the intima.

FIG. 8 illustrates an embodiment in which a single blade 56c moves from a nested position within or adjacent to stripping ring 34c to the cutting position of FIG. 8 to cut a portion of intima 26. The complete cut is made by rotating stripping ring 34c about 90° to 180° to completely sever intima 26 as suggested by arrow 58c.

Figure 9:
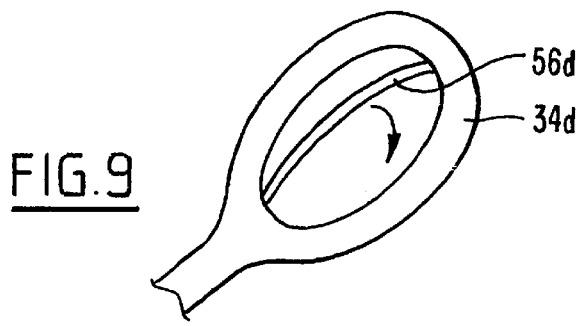
FIG. 9 illustrates a further embodiment of the invention in which a single curved blade is pivotally mounted at either end to opposite sides of the stripping ring so that when actuated, the curved blade cuts the intima in a scooping fashion.
Figure 9A:

FIGS. 9 and 9A illustrate a further embodiment of the invention in which a single curved blade 56d is pivotally mounted at either end to opposite ends of stripping ring 34d. Blade 56d is pivoted about 180° from a position aligned with one side of the stripping ring 34d to the other side of stripping ring 34d to create a curved, scooping-motion cut through intima 26.

Figure 10:
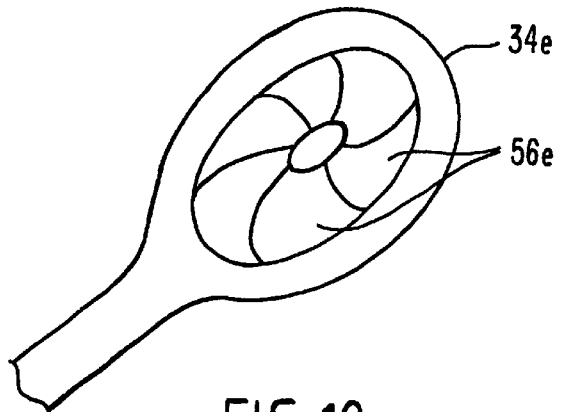
FIG. 10 is a simplified view showing an embodiment in which a series of small blades arranged in an iris pattern move inwardly from a retracted position within the ring stripper to sever the intima passing through the ring stripper.

Turning now to FIG. 10, stripping ring 34e is shown to have a number of small camera iris-type of blades 56e. Blades 56e move from a retracted position, providing a substantially unobstructed interior of stripping ring 34e, to an extended, cutting position shown in FIG. 10, at which point blades 56e have severed intima 26 passing through stripping ring 34e.

Figure 11:
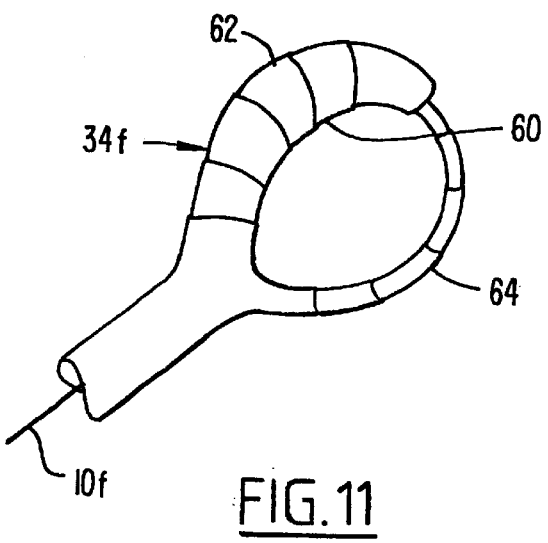
FIGS. 11 and 11A are views of a final embodiment of the invention in which the ring stripper is a segmented, telescoping ring stripper, at least a portion of the inner edge of the telescoping stripping ring is sharpened so that when moved from the expanded condition of FIG. 11 to the fully retracted condition of FIG. 11A, the sharp interior cutting edge severs the intima.
Figure 11A:
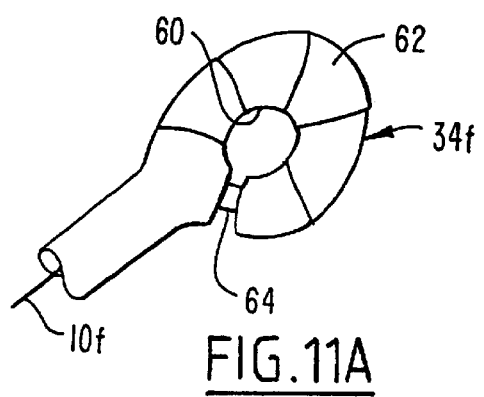

FIGS. 11 and 11A illustrate a telescoping stripping ring 34f having an inside cutting edge 60 formed on the segmented outer stripping ring portion 62. Outer portion 62 passes over the segmented inner portion 64 of stripping ring 34f. If necessary, stripping ring 34f can be rotated when in the cutting condition of FIG. 11A to completely sever intima 26. This can be done easily because the outside diameter of stripping ring 34f in the condition of FIG. 11A is smaller, thus not creating any undue stretching forces on the vessel.

Additional modifications and variations are conceivable within the range of the following claims.

What is claimed is:

1. A remote endarterectomy instrument comprising:

an elongate shaft having distal and proximal ends;

a ring, having an open interior, mounted at the distal end of the elongate shaft; and an intima cutter assembly comprising:

a cutting element, attached to the instrument at a position at the ring and being at least partially housed inside the ring, being movable along a cutting path across at least a portion of a cutting region angularly about said position at the ring, said cutting region passing through the open interior of said ring; and a cutting element actuator having a first end, located towards the proximal end of the shaft, operably coupled to the cutting element, said first end comprising a user-actuated manipulator to permit a user to cause the cutting element to move along the cutting path so as to cut an intima passing through the open interior of the ring.

2. The remote endarterectomy instrument of claim 1 wherein the elongate shaft is tubular.

3. The remote endarterectomy instrument of claim 1 wherein said cutting element comprises a movable generally flat cutting blade.

4. The remote endarterectomy instrument of claim 1 wherein the cutting element comprises a movable generally flat blade carried by the ring, said blade movable by the cutting element actuator from a first position to an extended, cutting position.

5. The remote endarterectomy instrument of claim 4 wherein the first position is adjacent said ring.

6. The remote endarterectomy instrument of claim 1 wherein the ring comprises first and second sides on opposite sides of said ring.

7. The remote endarterectomy instrument of claim 6 wherein the cutting element comprises a generally flat blade movable by the cutting element actuator from a first position in contact with said first side to a second position spaced apart from the first and second sides.

8. The remote endarterectomy instrument of claim 6 wherein the cutting element comprises a generally flat blade movable by the cutting element actuator from a first position adjacent a first side to a second position adjacent the second side.

9. The remote endarterectomy instrument of claim 1 wherein said ring is an intima stripping ring.

10. A remote endarterectomy instrument comprising:
an elongate shaft having distal and proximal ends;
a ring, having an open interior, mounted at the distal end of the elongate shaft;
said ring being a telescoping, collapsible ring having an inner cutting edge which constitutes a cutting element, the cutting element being movable along a cutting path across at least a portion of a cutting region, said cutting region passing through the open interior of said ring; and
a cutting element actuator having a first end, located towards the proximal end of the shaft, operably coupled to the cutting element, said first end comprising a user-actuated manipulator to permit a user to collapse said ring to cause the cutting element to move along the cutting path so as to cut an intima passing through the open interior of the ring.

11. A method for removing a length of intima from a blood vessel of a patient comprising the following steps:
making a singular incision in a blood vessel;
inserting a ring of an endarterectomy instrument through the incision and between the wall of the blood vessel and the intima of the blood vessel;
moving the ring a distance along the blood vessel along a length of intima between the length of intima and the vessel wall while a proximal portion of the instrument remains outside of the patient;
remotely severing the length of intima at the ring by manipulating the proximal portion of the instrument while the proximal portion of the instrument remains outside of the patient thereby to cause a cutting element to pass at least partially across an open interior of the ring; and
removing the severed length of intima and the ring from the patient through said singular incision.

12. The method according to claim 11 wherein said severed length of intima and the ring are simultaneously removed from the patient.

13. The method according to claim 11 wherein the inserting step is carried out using a ring stripper as said instrument with said ring being a stripping ring, and wherein the moving step is carried out using the stripping ring to loosen the length of intima from the vessel wall.

14. A method for removing a length of intima from a blood vessel of a patient comprising the following steps:
making an incision in a blood vessel;
inserting dual rings located adjacent one another at one end of an endarterectomy instrument through the incision and between the wall of the blood vessel and the intima of the blood vessel, at least one of said dual rings comprising an internal cutting edge;
moving the rings a distance along the blood vessel along a length of intima between the length of intima and the vessel wall while a proximal portion of the instrument remains outside of the patient;
remotely severing the length of intima at the rings from the proximal portion of the instrument while the proximal portion of the instrument remains outside of the patient; and
removing the severed length of intima and the rings from the patient.

15. A method for removing a length of intima from a blood vessel of a patient comprising the following steps:
making an incision in a blood vessel;
inserting a ring of an endarterectomy instrument through the incision and between the wall of the blood vessel and the intima of the blood vessel;
moving the ring a distance along the blood vessel along a length of intima between the length of intima and the vessel wall while a proximal portion of the instrument remains outside of the patient;
remotely severing the length of intima at the ring from the proximal portion of the instrument while the proximal portion of the instrument remains outside of the patient by pulling on an intima severing wire to move the intima severing wire from an initial position in contact with said ring; and removing the severed length of intima and the ring from the patient.

16. The method according to claim 15 wherein the pulling step moves the intima severing wire against the intima with a sawing motion.

17. A method for removing a length of intima from a blood vessel of a patient comprising the following steps:
making an incision in a blood vessel;
inserting a ring of an endarterectomy instrument through the incision and between the wall of the blood vessel and the intima of the blood vessel;
moving the ring a distance along the blood vessel along a length of intima between the length of intima and the vessel wall while a proximal portion of the instrument remains outside of the patient;
remotely severing the length of intima at the ring from the proximal portion of the instrument while the proximal portion of the instrument remains outside of the patient by moving a blade, initially positioned in contact with the ring, against the intima so to sever the intima; and removing the severed length of intima and the ring from the patient.

18. The method according to claim 17 wherein the blade moving step further comprises the step of rotating the ring at least part way around the intima.

19. A remote endarterectomy instrument comprising:

an elongate shaft having distal and proximal ends;

a ring, having an open interior, mounted at the distal end of the elongate shaft;

an intima cutter assembly comprising:

a cutting element, located at the ring, movable along a cutting path across at least a portion of a cutting region, said cutting region passing through the open interior of said ring, the cutting element comprising an intima severing wire; and a cutting element actuator having a first end, located towards the proximal end of the shaft, operably coupled to the cutting element, said first end comprising a user-actuated manipulator to permit a user to cause the cutting element to move along the cutting path so as to cut an intima passing through the open interior of the ring; and the ring comprising a groove facing the open interior and the intima-severing wire is locatable within said groove prior to actuating the cutting element actuator.

20. The remote endarterectomy instrument of claim 19 wherein the intima-severing wire has a smooth cutting surface.

21. The remote endarterectomy instrument of claim 19 wherein the intima-severing wire has a roughened cutting surface.

22. The remote endarterectomy instrument of claim 19 wherein said cutting element actuator comprises an actuator wire extending from the intima-severing wire.

23. The remote endarterectomy instrument of claim 22 wherein said elongate shaft is tubular and the actuator wire passes through said tubular elongate shaft.

24. A remote endarterectomy instrument comprising:

an elongate shaft having distal and proximal ends;

a ring, having an open interior, mounted at the distal end of the elongate shaft; and an intima cutter assembly comprising:

a cutting element, located at the ring, movable along a cutting path across at least a portion of a cutting region, said cutting region passing through the open interior of said ring;

a cutting element actuator having a first end, located towards the proximal end of the shaft, operably coupled to the cutting element, said first end comprising a user-actuated manipulator to permit a user to cause the cutting element to move along the cutting path so as to cut an intima passing through the open interior of the ring; and the cutting element comprising a set of iris blades movably mounted to the ring for movement by the cutting element actuator between an open position, at which said open interior is substantially open, and a closed position, at which said open interior is at least substantially covered by said iris blades.

25. A method for removing a length of intima from a blood vessel of a patient comprising the following steps:

making an incision in a blood vessel;

inserting dual rings of an endarterectomy instrument through the incision and between the wall of the blood vessel and the intima of the blood vessel, at least one of said dual rings comprising an internal cutting edge;

moving the rings a distance along the blood vessel along a length of intima between the length of intima and the vessel wall while a proximal portion of the instrument remains outside of the patient;

remotely severing the length of intima at the ring from the proximal portion of the instrument by sliding said dual rings against one another; and removing the severed length of intima and the dual rings from the patient.

26. A remote endarterectomy instrument comprising:

an elongate shaft having distal and proximal ends;

a ring, having an open interior, mounted at the distal end of the elongate shaft; and an intima cutter assembly comprising:

a cutting element movable along a cutting path across at least a portion of a cutting region, said cutting region passing through the open interior of said ring; and a cutting element actuator having a first end, located towards the proximal end of the shaft, operably coupled to the cutting element, said first end comprising a user-actuated manipulator to permit a user to cause the cutting element to move along the cutting path so as to cut an intima passing through the open interior of the ring, wherein the cutting element comprises a retractable blade carried by the shaft, said blade movable by the cutting element actuator from a retracted position to an extended, cutting position.

27. The remote endarterectomy instrument of claim 26, wherein the retracted position is within the elongate shaft.

* * * * *